United States Patent
Myx

(10) Patent No.: US 8,788,241 B2
(45) Date of Patent: Jul. 22, 2014

(54) SYSTEM FOR INSPECTING A HULL OF A SHIP AND ASSOCIATED METHOD

(75) Inventor: Olivier Myx, Toulon (FR)

(73) Assignee: DCNS, Paris (FR)

( * ) Notice: Subject to any disclaimer, the term of this patent is extended or adjusted under 35 U.S.C. 154(b) by 860 days.

(21) Appl. No.: 13/001,787

(22) PCT Filed: Jun. 26, 2009

(86) PCT No.: PCT/FR2009/051230
§ 371 (c)(1),
(2), (4) Date: Jan. 21, 2011

(87) PCT Pub. No.: WO2010/004181
PCT Pub. Date: Jan. 14, 2010

(65) Prior Publication Data
US 2011/0191061 A1  Aug. 4, 2011

(30) Foreign Application Priority Data
Jun. 30, 2008 (FR) ...................................... 08 54396

(51) Int. Cl.
*G01C 9/00* (2006.01)
*G01N 29/04* (2006.01)
*G01B 17/02* (2006.01)
*B63B 9/00* (2006.01)

(52) U.S. Cl.
CPC .... *G01N 29/043* (2013.01); *G01N 2291/02854* (2013.01); *G01B 17/02* (2013.01); *B63B 9/00* (2013.01)
USPC ........................................................ 702/154

(58) Field of Classification Search
CPC .................. G01N 29/043; G01N 2291/02854; G01B 17/02; B63B 9/00
USPC ........................................................ 702/154
See application file for complete search history.

(56) References Cited

U.S. PATENT DOCUMENTS

| | | | | |
|---|---|---|---|---|
| 5,947,051 A | * | 9/1999 | Geiger | 114/313 |
| 6,191,732 B1 | * | 2/2001 | Carlson et al. | 342/357.3 |
| 6,314,341 B1 | * | 11/2001 | Kanayama | 701/1 |
| 6,317,387 B1 | * | 11/2001 | D'Amaddio et al. | 367/129 |
| 7,039,521 B2 | * | 5/2006 | Hortner et al. | 701/436 |
| 8,024,066 B2 | * | 9/2011 | Reverte et al. | 700/245 |
| 2007/0029125 A1 | | 2/2007 | Jeswine et al. | |
| 2009/0301203 A1 | * | 12/2009 | Brussieux | 73/627 |

FOREIGN PATENT DOCUMENTS

FR    2 861 457 A1    4/2005
WO    2006/114485 A1    11/2006

OTHER PUBLICATIONS

International Search Report, dated Feb. 11, 2010, from corresponding PCT application.

* cited by examiner

*Primary Examiner* — Tung S Lau
*Assistant Examiner* — Xiuquin Sun
(74) *Attorney, Agent, or Firm* — Young & Thompson

(57) ABSTRACT

A system for inspecting the hull of a vessel includes a movable machine which moves on the hull and a positioning element to determine an instantaneous position of the machine in a reference point. The positioning element includes: —first and second coaxial encoding wheels separated from each other by an inter-wheel spacing and in contact with the hull, and are capable of measuring first and second linear movements of the machine; —first and second inclinometers arranged so as to measure inclinations, relative to a reference direction, of a first axis and a second axis of a frame of reference linked to the machine; and, —a processing element, which receives data measured in order to calculate a variation of the position of the machine in the frame of reference, and in order to integrate the successive position variations in order to obtain the instantaneous position of the machine.

20 Claims, 2 Drawing Sheets

SYSTEM FOR INSPECTING A HULL OF A SHIP AND ASSOCIATED METHOD

The invention relates to a system for inspecting the hull of a vessel of the type comprising a movable machine which is capable of moving on the surface of the hull of the vessel. More particularly, the invention relates to a positioning means which allows an instantaneous position of the machine to be obtained relative to a reference point.

BACKGROUND OF THE INVENTION

Inspection systems are known which comprise a remote-controlled automated machine which is capable of moving on the hull of a vessel. To this end, the movable machine is provided with a movement means which comprises an adhesion means which allows the machine to remain in contact with the hull, and a driving means for moving the machine on the surface of the hull of the vessel. The machine also carries on-board various types of sensor in order to carry out local measurements of characteristic physical values of the hull. The machine also comprises a positioning means which allows an instantaneous position to be obtained for the machine relative to a reference point which is preferably associated with the hull of the vessel. The association of a measurement of a physical value and the position of the machine at the time this measurement was carried out allows a map of the hull to be produced by moving the machine along a suitable trajectory.

Up to the present time, as described, for example, in document FR 2 861 457, the positioning means is a means for positioning under water or a means for positioning in the air. Consequently, the inspection system is used, on the submerged portion of the hull of a vessel, that is to say, below the water line of the vessel, or on the non-submerged portion, that is to say, above the water line.

A known means for positioning under water comprises an acoustic transmitter which is arranged on the movable machine, and two acoustic receivers which are submerged and fixed to two buoys floating on the surface of the water, respectively. The buoys, which are remote from each other, are positioned in an absolute manner by a system of the GPS type. The transmitter generates a periodic acoustic signal, and the time correlation of the signals received, at the buoys, by each of the receivers allows the position of the machine to be determined relative to the buoys by means of triangulation. Such a means for positioning under water offers a maximum precision of the order of 50 cm.

The use of such a means for positioning under water requires a free space at the side of the vessel in order to arrange the buoys remote from the hull in order to achieve maximum precision. This prevents the inspection system from being used at the side of the hull directed towards the quay. The vessel must be moved in order to make it carry out a half-turn, in order to release the side of the hull which is initially close to the quay when it is desirable to carry out an inspection.

A known means for positioning in the air uses a system of the DGPS type, between markers on the ground and an antenna placed on the movable machine. The maximum precision of such a means for positioning in the air is of the order of 50 cm.

Another known means for positioning in the air involves an optical device which comprises a reference station which is fixed to the ground and an optical transmitter which is fixed to the robot. The reference station automatically points to the transmitter and transmits the three-dimensional position thereof with a precision which is within centimeters.

The first two above-mentioned positioning means do not provide the precision required to carry out an inspection of the hull of a vessel in an effective manner. The same defect of the hull must be prevented from being mapped several times as having different positions owing to a lack of precision of the position measurements of the machine. Otherwise, this would lead to the overestimation of the gravity of this defect and the implementation of significant maintenance operations of the hull which might require the immobilisation of the vessel. Conversely, a significant defect must be prevented from being underestimated owing to the lack of precision of the positioning means. In this manner, the desirable precision with respect to the positioning of such an inspection system is in the order of 10 cm.

Furthermore, it is desirable to be able to inspect the hull of the vessel over the entire surface thereof, that is to say, both below and above the water line, using a single machine. To this end, it is necessary to provide a positioning system which operates both in air and in water. It is also desirable for such a positioning system to allow the machine to be positioned with the same precision both below and above the water line.

In order to carry out instantaneous measurements of the position of the machine both in air and in water, and with the same precision, one possible solution is to provide the machine with an inertial unit. The integration of the movements of the machine during its movement from a reference point allows the instantaneous position of the machine to be determined. However, for the desired precision, the cost of a suitable inertial unit is high. Furthermore, the significant volume and the mass of an inertial unit are incompatible with the correct operation of the machine which must remain light and compact in order to adhere to and move on the hull of the vessel.

SUMMARY OF THE INVENTION

An object of the invention is therefore to provide a system for inspecting the hull of a vessel which is provided with a means for positioning the movable machine which allows position measurements to be taken both above and below the water line of the vessel with a consistent and high level of precision, whilst having reduced operating cost.

To this end, the invention relates to a system for inspecting the hull of a vessel, of the type comprising a movable machine which is provided with a movement means which allows it to move on the surface of the hull of the vessel, the system further comprising a positioning means which allows an instantaneous position of the machine to be determined relative to a reference point. The positioning means comprises:
  first and second encoding wheels which are provided on the machine, which are coaxial and separated from each other by an inter-wheel spacing along a transverse axis perpendicular relative to a longitudinal movement axis of the machine, which are in contact with the hull of the vessel, and which are capable of measuring first and second instantaneous linear movements of the machine;
  first and second inclinometers which are provided on the machine and which are arranged so as to measure instantaneous inclinations, relative to a reference direction, of a first axis and a second axis of a frame of reference linked to the machine, respectively; and
  a processing means, which receives as inputs the first and second instantaneous linear movements and the first and second instantaneous inclinations and which is capable of calculating an instantaneous variation of the position of the machine in the frame of reference and which is capable of integrating the successive instantaneous position variations, from a known initial position, in order to determine an instantaneous position of the machine in the frame of reference.

According to specific embodiments of the invention, the inspection system comprises one or more of the following features, taken in isolation or according to any technically possible combination:
  the inspection system comprises at least one sensor for measuring a local value of a parameter which is characteristic of the hull of the vessel,
  the first axis is parallel with a longitudinal direction X of the machine and the second axis is parallel with a transverse direction Y of the machine, the first and second axes being orthogonal relative to a direction which is normal relative to the surface of the hull of the vessel,
  the reference direction of the inclinometers is a geographical vertical line,
  the machine is operated remotely, the inspection system comprising a remote control station which is in communication with the machine,
  the processing means is provided on-board the machine,
  the remote control station comprises the processing means,
  the system is capable of taking into account the measurements of the instantaneous orientation of the vessel relative to the reference point in order to determine an instantaneous position of the machine in a frame of reference which is linked to the hull of the vessel.

The invention also relates to a method for inspecting the hull of a vessel which implements the inspection system set out above and which comprises at least the steps of:
  placing the machine against the hull of a vessel and controlling its movement;
  measuring an instantaneous linear movement of the machine;
  measuring an instantaneous rotation of the machine about a direction Z normal relative to the surface of the hull of the vessel;
  measuring the first and second instantaneous inclinations of first and second axes linked to the machine relative to a frame of reference;
  processing the measured data in order to calculate a variation of the instantaneous position of the machine; then
  integrating the instantaneous position variations from a predetermined initial position, in order to determine an instantaneous position of the machine in the frame of reference.

The inspection method comprises one or more of the following features, taken in isolation or according to any technically possible combination:
  the measurements carried out are recorded by sensors with which the machine is provided, and each measurement is associated with the position at which the acquisition was made,
  the instantaneous orientation of the vessel is measured relative to the frame of reference in order to determine, from the variation of the instantaneous position of the machine relative to the frame of reference, the instantaneous position variation of the machine relative to a frame of reference which is linked with the hull of the vessel.

BRIEF DESCRIPTION OF THE DRAWINGS

The invention and the advantages thereof will be better understood from a reading of the following description, given purely by way of example and with reference to the appended drawings, in which.

DETAILED DESCRIPTION OF THE PREFERRED EMBODIMENTS

Figure 1:
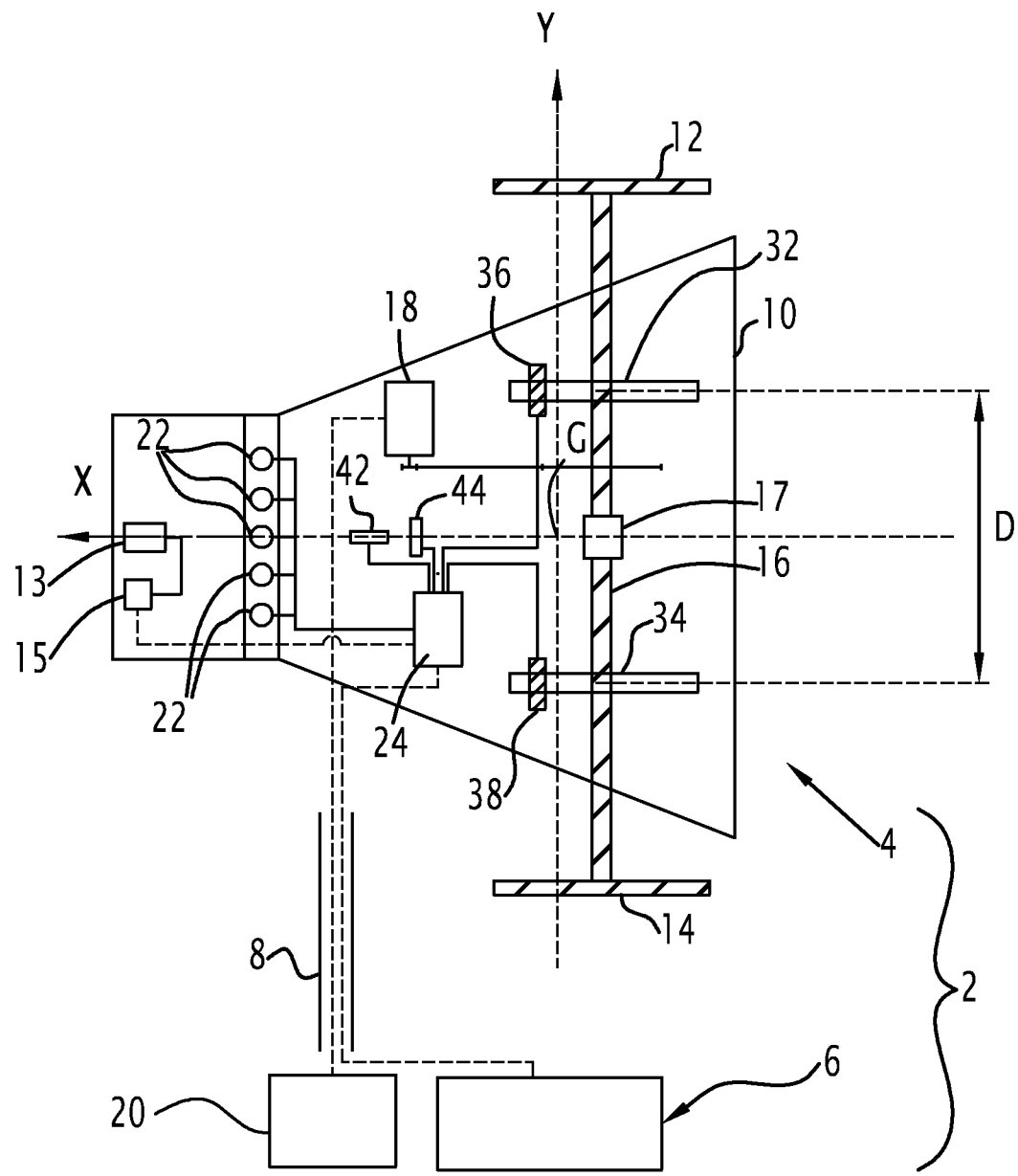
FIG. 1 is a schematic illustration of the system for inspecting the hull of a vessel.

With reference to FIG. 1, the inspection system 2 comprises a remote-controlled automated machine 4. To this end, the inspection system 2 comprises a control unit 6 which allows an operator to control the operation of the machine 4. The control unit 6 is connected to the machine 4 by a connection means which is an electrical cable which extends along an umbilical 8 or a radio communication means.

The machine 4 comprises a chassis 10 generally of parallelepipedal shape, a means which allows it to be held against the hull of a vessel and a movement means.

The movement means comprises two drive wheels 12 and 14 which are mounted at the ends of an axle 16. The movement means comprises a differential system 17 in order to allow the drive wheels 12 and 14 to rotate at different rotation speeds.

In order to locate the various elements which constitute the machine 4 and to define the orientation thereof in space, there is associated with the chassis 10 an orthonormal frame of reference X, Y, Z, which has, as its origin, the centre of gravity G of the machine 4. The transverse direction Y is parallel with the axle 16, the direction Z is normal relative to the surface of the hull and the longitudinal direction X is perpendicular relative to the directions Y and Z.

The movement means also comprises a front steering wheel 13. A remote-controlled actuation means 15 is capable of turning the front steering wheel 13 through 360° about an axis parallel with the direction Z, so as to rotate the chassis 10 of the machine 4 so that it travels over the hull of the vessel.

The movement means further comprises a means for driving the axle 16, in order to cause the machine 4 to move in the longitudinal direction X. The drive means comprises, for example, an electric motor 18 which is supplied with electrical current by a battery 20. Preferably, the battery 20 is not arranged inside the chassis 10 but remotely, the electrical energy being supplied from the battery 20 to the motor 18 via a supply cable which extends along the umbilical 8.

The means for holding the machine 4 against the hull of the vessel comprises adhesion means (not illustrated) which use magnetic forces to press the machine 4 against the hull of the vessel, whilst allowing the wheels of the movement means to travel over the surface of the hull.

The machine 4 carries on-board various types of sensor which are intended to carry out measures on the hull of the vessel. These sensors are, for example, ultrasound sensors which allow the local thickness of the hull of the vessel to be measured. In FIG. 1, these thickness sensors are generally designated 22.

The inspection system 2 comprises a processing means which has, inter alia, a calculation unit, memory means and an input/output interface. Preferably, the processing means 24 is provided on-board the machine 4, but could be located remotely in a variant, in the region of the control unit 6. The various sensors, such as the sensors 22 with which the machine 4 is provided, are connected to the processing means 24 by means of the input/output interface.

The inspection system 2 comprises a positioning means which is capable of operating, with the same precision, in the air and in water.

The positioning means comprises, on the machine 4, first and second encoding wheels 32 and 34 which are mounted so as to rotate freely on the axle 16. The encoding wheels 32 and 34 are independent of the drive wheels 12 and 14 so as not to be sensitive to the sliding of the drive wheels, in particular during a rotation of the machine 4 about a direction Z which is normal relative to the surface of the hull.

The first and second encoding wheels 32 and 34 are separated from each other by a predetermined inter-wheel spacing D and are in contact with the hull of the vessel without sliding. First and second optical sensors 36 and 38 are arranged in the region of the first and second encoding wheels 32 and 34, respectively, so as to generate an electrical signal which is transmitted in the direction of the processing means 24, when a mark arranged on the associated encoding wheel passes in front of the sensor in question. The two electrical signals correspond to first and second linear movements, respectively.

The mean of the first and second linear movements represents an instantaneous elementary translation of the machine 4 in the longitudinal direction X. The difference between the first and second linear movements, taking into account the inter-wheel spacing D, represents an instantaneous elementary rotation of the machine 4 about the direction Z which is normal relative to the surface of the hull.

The positioning means also comprises first and second inclinometers 42 and 44. The first inclinometer 42 is arranged so as to measure the instantaneous inclination between the longitudinal axis X of the chassis 10 and a reference direction Zref which is preferably a geographical vertical line. The second inclinometer 44 is arranged so as to measure an instantaneous inclination of the transverse axis Y of the chassis 10, preferably relative to the same reference direction Zref. The person skilled in the art will appreciate that the first and second inclinometers 42 and 44 can be arranged differently, as long as they allow two instantaneous inclination measurements of two axes which define a characteristic plane to be obtained.

The first and second inclinometers 42 and 44 are connected to the processing means 24 to which they transmit the electrical signals which they produce in order to determine the inclination of the axes X and Y relative to the reference direction. The processing means 24 can, for example, operate by means of sampling. In this instance, the difference between the inclination measurement at a given time and the inclination measurement at an immediately following time, that is to say, at the following sampling time of the processing means 24, allows a measurement to be obtained of the instantaneous inclination variation of an axis relative to the reference direction.

The instantaneous elementary movement in the longitudinal direction X, the instantaneous elementary rotation of the machine 4 about the direction Z normal relative to the surface of the hull, and the instantaneous inclination variations in the longitudinal direction X and transverse direction Y allow the calculation, between two successive sampling times, of an instantaneous position variation vector of the machine relative to a frame of reference Xref, Yref, Zref fixed in space.

Since it is desirable to produce a map of the hull of the vessel, it is necessary to know the instantaneous position variation of the machine 4 relative to the vessel. In order to move from the frame of reference Xref, Yref, Zref to a frame of reference X0, Y0, Z0 linked to the hull of the vessel, it is necessary to determine the instantaneous orientation of the vessel relative to the frame of reference Xref, Yref, Zref.

To this end, there is fixed to the vessel an assembly 60 comprising reference inclinometers and means for transmitting the measurements carried out, for example, to the processing means 24. The reference inclinometers which are fixedly joined to the hull, measure, at all times, the rolling and pitching inclinations of the vessel relative to the frame of reference. These measurements allow the processing means 24 to determine the instantaneous orientation of the frame of reference X0, Y0, Z0 linked to the hull relative to the frame of reference Xref, Yref, Zref. Then, from the position variation vector of the machine 4 relative to the frame of reference and in the knowledge of the instantaneous orientation of the frame of reference linked to the hull relative to the frame of reference, the processing means 24 determines an instantaneous position variation vector of the machine 4 relative to the frame of reference X0, Y0, Z0 linked to the hull.

In a variant, the vessel is provided with a means for determining the instantaneous orientation thereof, such as an inertial unit, whose measurements are transmitted to the processing means 24 in order to determine the movement of the machine relative to the hull of the vessel.

In this manner, the inspection method can be carried out not only when the vessel to be inspected is still, in dock, but also when it is moving, for example, at sea.

Figure 2:
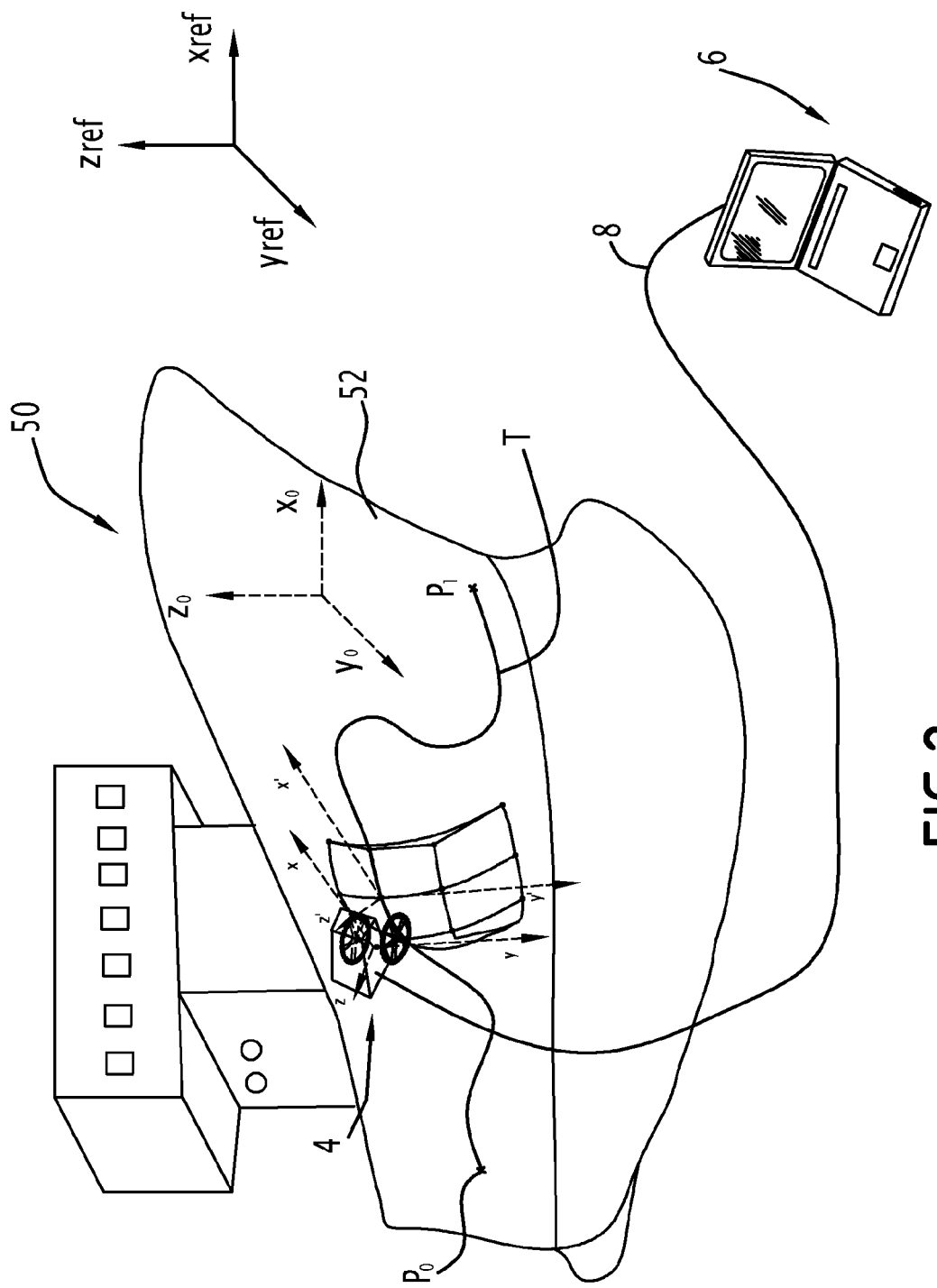
FIG. 2 illustrates the inspection method implementing the system of FIG. 1.

With reference to FIG. 2, the use of the machine 4 will now be described in order to establish a map of the thickness defects of the hull 52 of a vessel 50.

First of all, the machine 4 is placed at a point P0 of the hull 52. The point P0 has a known position in the frame of reference X0, Y0, Z0 linked to the hull. For example, the point P0 is the rear perpendicular of the vessel 50.

Then, the movement of the machine 4 is remotely actuated by an operator using the station 6. Between two successive sampling times, the reference point linked to the machine 4, indicated in FIG. 2 by the directions X, Y and Z at the preceding sampling time and by the directions X', Y' and Z' at the following sampling time, has moved. By adapting the sampling time and the movement speed in accordance with the precision desired, the processing means 24 calculates in real time the instantaneous position variation vector of the machine relative to the frame of reference. Taking into account the instantaneous orientation of the vessel relative to the frame of reference, the processing means 24 calculates, in real time, the instantaneous position variation vector of the machine relative to the frame of reference linked to the hull. The person skilled in the art will know the mathematical processing steps which will allow the instantaneous position variation vectors to be calculated from the measured data of inclination, rotation and translation.

Then, the processing means 24 integrates relative to time the instantaneous position variation vector of the machine 4 relative to the frame of reference linked to the hull and taking into consideration the position of the starting point P0, in order to determine the instantaneous position of the machine 4 relative to the frame of reference linked to the hull. In this manner, the trajectory T followed by the machine 4 during its movement on the hull of the vessel is gradually reconstructed in three dimensions.

By causing the machine 4 to follow a succession of trajectories T along the hull 52, and preferably trajectories T which intersect at a right angle, the surface of the hull 52 is reconstructed in three dimensions.

Optionally, during the movement of the machine 4, it is possible to adjust the instantaneous position of the machine 4 in the frame of reference linked to the hull by causing it to pass via a point P1 of the hull 52 whose position in the frame of reference linked to the hull is completely known. For example, the machine 4 may follow a trajectory T which extends via the intermediate point P1 which is the front perpendicular of the hull 52.

In order to carry out the mapping of the defects of the hull, the processing means 24 records, at each sampling, the position of the machine 4 and the value(s) measured by the sensors 22. In a variant, instead of associating a position with a value, there is associated, on the one hand, a position with a measuring time of this position and, on the other hand, a value with a measuring time for this value. This method of dating data uses a time signal supplied by a clock. This is, for example, the time signal supplied by a GPS system.

In a variant, the data processing, instead of being carried out by an on-board processing means of the machine, is carried out by a processing means which is provided for this purpose in the remote control unit. The processing can also be carried out in real time or in deferred time.

The person skilled in the art will find that the means used according to the invention are robust and that they function both under water and in air. The precision relating to the instantaneous position of the machine is 0.05%.

The method for inspecting the hull of a vessel which has been set out allows a grid to be produced of the surface of the hull of the vessel inspected which, in accordance with the sampling time, may have a pitch much less than the 50 cm generally required by the standards for quality control of the state of vessel hulls.

Advantageously, the inspection method allows the significant demands to be complied with which are required for the precision of maps which allow the control of hulls of submarines.

Advantageously, since the hull maps produced by carrying out the inspection method have a high degree of precision, the inspection method can be carried out after the vessel has been loaded in order to measure the instantaneous gauge of the vessel, that is to say, all of the wet surface of the hull of the loaded vessel. This has an advantage, for example, if the vessel takes a channel whose passage rate is calculated based on the gauge of the vessel. Up to the present time, it is the theoretical gauge of the vessel that is used. However, by implementing the present invention, the instantaneous gauge could be used.

The invention claimed is:

1. A system (2) for inspecting the hull (52) of a vessel (50), comprising:
    a movable machine (4) with a movement means configured for movement on the surface of the hull of the vessel; and
    a positioning means that determines a position of the machine relative to a reference point fixed in space, the positioning means comprising
        first and second encoding wheels (32, 34) which are provided on the machine, which are coaxial and separated from each other by an inter-wheel spacing (D) along a transverse axis (4) perpendicular relative to a longitudinal movement axis (X) of the machine, which are in contact with the hull of the vessel, and which are capable of measuring first and second instantaneous linear movements of the machine,
        first and second inclinometers (42, 44) which are provided on the machine and which are arranged so as to measure instantaneous inclinations, relative to a frame of reference direction, of a first axis and a second axis of a frame of reference linked to the machine, respectively, and
        a processing means (24) which receives, as inputs, the first and second instantaneous linear movements and the first and second instantaneous inclinations and which is capable of calculating an instantaneous variation of the position of the machine in the frame of reference linked to the machine, and which is capable of integrating successive instantaneous position variations, from a known initial position (P0), in order to determine an instantaneous position of the machine in the frame of reference fixed in space.

2. The inspection system according to claim 1, further comprising:
    at least one sensor (22) for measuring a local value of a parameter which is characteristic of the hull of the vessel.

3. The inspection system according to claim 2, wherein the first axis is parallel with a longitudinal direction (X) of the machine (4) and in that the second axis is parallel with a transverse direction (Y) of the machine (4), the first and second axes being orthogonal relative to a direction which is normal relative to the surface of the hull of the vessel.

4. The inspection system according to claim 2, wherein the reference direction of the inclinometers (42, 44) is a geographical vertical line.

5. The inspection system according to claim 2, further comprising:
    a remote control station (6) which is in communication with the machine.

6. The inspection system according to claim 2, wherein the processing means (24) is provided on-board the machine (4).

7. The inspection system according to claim 1, wherein the first axis is parallel with a longitudinal direction (X) of the machine (4) and in that the second axis is parallel with a transverse direction (Y) of the machine (4), the first and second axes being orthogonal relative to a direction which is normal relative to the surface of the hull of the vessel.

8. The inspection system according to claim 7, wherein the reference direction of the inclinometers (42, 44) is a geographical vertical line.

9. The inspection system according to claim 7, further comprising:
    a remote control station (6) which is in communication with the machine.

10. The inspection system according to claim 7, wherein the processing means (24) is provided on-board the machine (4).

11. The inspection system according to claim 1, wherein the reference direction of the inclinometers (42, 44) is a geographical vertical line.

12. The inspection system according to claim 11, further comprising:
    a remote control station (6) which is in communication with the machine.

13. The inspection system according to claim 11, wherein the processing means (24) is provided on-board the machine (4).

14. The inspection system according to claim 1, wherein the inspection system (2) further comprises a remote control station (6) which is in communication with the machine.

15. The inspection system according to claim 14, wherein the remote control station (6) comprises the processing means.

16. The inspection system according to claim 1, wherein the processing means (24) is provided on-board the machine (4).

17. The inspection system according to claim 1, wherein the positioning means is capable of taking into account the measurements of the instantaneous orientation of the vessel relative to the reference point in order to determine an instantaneous position of the machine in a frame of reference (X0, Y0, Z0) which is linked to the hull of the vessel.

18. A method for inspecting the hull of a vessel, comprising:
- providing an inspection system (2) according to claim 1;
- placing the machine against the hull of a vessel and controlling its movement;
- measuring an instantaneous linear movement of the machine (4);
- measuring an instantaneous rotation of the machine about a direction (Z) normal relative to the surface of the hull (52) of the vessel (50);
- measuring the first and second instantaneous inclinations of first and second axes linked to the machine relative to a reference direction;
- processing the measured data in order to calculate a variation of the instantaneous position of the machine in a frame of reference; and then
- integrating the instantaneous position variations from a predetermined initial position (P0), in order to determine an instantaneous position of the machine in the frame of reference fixed in space.

19. The method according to claim 18, wherein the measurements carried out are recorded by sensors with which the machine is provided, and each measurement is associated with the position at which the acquisition was made.

20. The method according to claim 18, wherein the instantaneous orientation of the vessel is measured relative to the frame of reference in order to determine, from the variation of the instantaneous position of the machine relative to the frame of reference, the instantaneous position variation of the machine relative to a frame of reference which is linked with the hull of the vessel.

* * * * *